United States Patent
Narusawa (10) Patent No.: US 9,138,153 B2
(45) Date of Patent: Sep. 22, 2015

(54) SPHYGMOGRAPH AND SIGNAL PROCESSING METHOD

(75) Inventor: Atsushi Narusawa, Hino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 732 days.

(21) Appl. No.: 13/426,090

(22) Filed: Mar. 21, 2012

(65) Prior Publication Data

US 2012/0249766 A1    Oct. 4, 2012

(30) Foreign Application Priority Data

Mar. 29, 2011  (JP) ................. 2011-071870

(51) Int. Cl.
 *H04N 7/18* (2006.01)
 *A61B 5/024* (2006.01)
 *A61B 5/00* (2006.01)

(52) U.S. Cl.
 CPC ......... *A61B 5/02438* (2013.01); *A61B 5/02416* (2013.01); *A61B 5/6824* (2013.01); *A61B 5/6826* (2013.01)

(58) Field of Classification Search
 USPC .............................................. 348/77, E7.085
 See application file for complete search history.

(56) References Cited

U.S. PATENT DOCUMENTS

| 4,955,379 | A  |   | 9/1990  | Hall |
|-----------|----|---|---------|------|
| 6,095,984 | A  | * | 8/2000  | Amano et al. ............... 600/500 |
| 6,701,170 | B2 |   | 3/2004  | Stetson |
| 2006/0084879 | A1 | | 4/2006 | Nazarian et al. |
| 2008/0249423 | A1 | | 10/2008 | Kitajima et al. |
| 2010/0198087 | A1 | | 8/2010 | Takahashi et al. |
| 2012/0004519 | A1 | | 1/2012 | Nazarian et al. |

FOREIGN PATENT DOCUMENTS

| CN | A-101039617 | 9/2007 |
| JP | A-2008-253579 | 10/2008 |
| JP | A-2010-172645 | 8/2010 |
| JP | A-2011-104124 | 6/2011 |
| JP | A-2011-217784 | 11/2011 |

* cited by examiner

*Primary Examiner* — Hung Dang
*Assistant Examiner* — Girumsew Wendmagegn
(74) *Attorney, Agent, or Firm* — Oliff PLC (57) ABSTRACT

A sphygmograph includes: a first signal processing unit and a second signal processing unit that process pulse waves obtained from a pulse sensor unit; a signal processing selection unit that determines whether or not to cause the second signal processing unit to also operate at the same time as the first signal processing unit; and a save data generation unit that saves, of the signal processing results from the first signal processing unit and the second signal processing unit, the signal processing result selected by the signal processing selection unit.

6 Claims, 7 Drawing Sheets

EXAMPLE OF SERIES OF POLE TIMES

| |
|---|
| 10:21:51.020 |
| 10:21:51.600 |
| 10:21:52.140 |
| 10:21:52.700 |
| 10:21:53.160 |
| 10:21:53.680 |
| 10:21:54.200 |
| 10:21:54.740 |
| 10:21:55.260 |
| ... |
| 10:21:59.380 |
| 10:21:59.900 |

FIG. 6

EXAMPLE OF SERIES OF PEAK TIMES

| | |
|---|---|
| 6-A → | 10:21:50.000 |
| | 10:21:51.020 |
| | 10:21:52.140 |
| | 10:21:53.160 |
| | 10:21:54.200 |
| | 10:21:55.260 |
| | 10:21:56.300 |
| | 10:21:57.320 |
| | 10:21:58.380 |
| 6-X → | 10:21:59.380 |

[PREVIOUS FINAL PEAK TIME] 10:21:59.380

FIG. 7

EXAMPLE OF SERIES OF RR INTERVALS

| |
|---|
| 1.020 |
| 1.120 |
| 1.020 |
| 1.040 |
| 1.060 |
| 1.040 |
| 1.020 |
| 1.060 |
| 1.000 |

SPHYGMOGRAPH AND SIGNAL PROCESSING METHOD

BACKGROUND

1. Technical Field

The present invention relates to sphygmographs and to signal processing methods used in such sphygmographs.

2. Related Art

Internal states of the human body can be discovered by using a photoelectric sensor that emits light at a specific wavelength and measures the reflected or transmitted light in order to analyze obtained waveforms. As one example, information related to the pulse, blood, and so on in a human body can be obtained by utilizing the light-absorbing characteristics of blood in areas of the living body in which blood is present.

For instance, if a pulse wave can be accurately captured, information regarding cardiac movement can be obtained. The pulse wave interval is sometimes used in the same manner as the RR interval of an electrocardiogram, and although the pulse wave interval is used in judging partial arrhythmia, it can also be used to derive an autonomic nerve index and determine sleep states by analyzing frequencies, if long-term data can be obtained; in addition, fluctuation in the RR interval is also sometimes used to analyze heart function.

JP-A-2008-253579 attempts to acquire a pulse peak interval that corresponds to an electrocardiogram RR interval by obtaining a sphygmograph using a photoelectric sensor. Furthermore, a noise removal process is carried out in order to remove reflected waves, notches, and so on that result in noise.

However, when, in the stated method, the signal processing, or in other words, the DC component of the photoelectric sensor output signal is unstable, such as when the measurement subject is not at rest, the noise removal is insufficient for the noise resulting from body movements; it is necessary to employ signal processing that can handle high-frequency noise, low-frequency noise, and changes in the DC component. As examples of such a signal processing method, an adaptive filter that extracts a spectrum unique to pulse waves (for example, see U.S. Pat. No. 4,955,379), applying independent component analysis (for example, see U.S. Pat. No. 6,701,170), and so on have been proposed.

However, in an integrated device (sphygmograph) that has limited processing capabilities and power performance, the signal processes described in U.S. Pat. No. 4,955,379 and U.S. Pat. No. 6,701,170 are complicated in the case where a pulse is to be measured continuously on a daily basis. Accordingly, these signal processes cannot be carried out to a sufficient degree in devices with low computational processing capabilities, such as such integrated devices.

With respect to this point, the signal processing disclosed in JP-A-2008-253579 is simple and can thus be implemented, but doing so is problematic in that sufficient processing for noise cannot be carried out, which makes the measurement results unreliable. It is therefore necessary to save a plurality of signal processing results that complement one another, but the storage capacity for saving such results is limited in integrated devices.

SUMMARY

Having been conceived in order to solve at least one of the aforementioned problems, the invention can be implemented as the following aspects or application examples.

A sphygmograph according to this aspect includes: a photoelectric sensor unit that detects an amount of light emitted from a human body and outputs an electrical signal; a first signal processing unit that performs a signal process on the signal outputted from the photoelectric sensor unit; a second signal processing unit that performs a signal process on the signal outputted from the photoelectric sensor unit according to a different processing format from that of the first signal processing unit; a signal processing selection unit that determines whether or not to cause the second signal processing unit to operate along with the first signal processing unit at the same time; and a signal processing result saving unit that saves, of signal processing results of the first signal processing unit and the second signal processing unit, a signal processing result selected by the signal processing selection unit.

According to this aspect, the first signal processing unit carries out processing using the change in the amount of light emitted from the human body detected by the photoelectric sensor unit as an electrical signal and saves the result of the processing in the signal processing result saving unit, and when necessary, the signal processing selection unit causes the second signal processing unit to operate so as to process the electrical signal using the second signal processing unit; this makes it possible to save the signal processing result at the same time as the first signal processing result. Accordingly, the sphygmograph according to this aspect can continually save the signal processing result from the first signal processing unit, and can also save the result from the second signal processing unit when necessary.

In the sphygmograph according to the aforementioned aspect, it is preferable that the signal processing selection unit have a motion sensor unit that detects a motion amount of the human body and outputs a signal, and a motion signal processing unit that performs a signal process on the signal outputted from the motion sensor unit. The signal processing selection unit determines whether or not to cause the second signal processing unit to operate along with the first signal processing unit at the same time in accordance with a value outputted by the motion signal processing unit.

According to this aspect, the motion signal processing unit carries out signal processing on the motion amount using the motion amount of the human body detected by the motion sensor unit as an input signal, and the signal processing selection unit can determine whether or not to cause the second signal processing unit to also operate at the same time as the first signal processing unit using the signal outputted by the motion signal processing unit. Accordingly, the sphygmograph according to this aspect is not only capable of continually saving the signal processing result of the first signal processing unit, but can also operate the second signal processing unit in accordance with the movement in the human body and save the signal processing result of the second signal processing unit at the same time as the first signal processing result; this makes it possible to use results of signal processing that is more robust to bodily movements, and also makes it possible to verify and correct the first signal processing result.

In the sphygmograph according to the aforementioned aspects, it is preferable that the signal processing selection unit have a shift sensor unit that detects an amount by which the photoelectric sensor shifts from the human body and outputs a signal, and a shift signal processing unit that performs a signal process on the signal outputted from the shift sensor unit. The signal processing selection unit determines whether or not to cause the second signal processing unit to operate along with the first signal processing unit at the same time in accordance with a value outputted by the shift signal processing unit.

According to this aspect, the shift signal processing unit carries out signal processing on the shift amount using the shift amount of the sensor detected by the shift sensor unit as an input signal, and the signal processing selection unit can determine whether or not to cause the second signal processing unit to also operate at the same time as the first signal processing unit using the signal outputted by the shift signal processing unit. Accordingly, the sphygmograph according to this aspect is not only capable of continually saving the signal processing result of the first signal processing unit, but can also operate the second signal processing unit in accordance with the shift in the photoelectric sensor and save the signal processing result of the second signal processing unit at the same time as the first signal processing result; this makes it possible to verify and correct the processing result of the first signal processing unit.

In the sphygmograph according to the aforementioned aspects, it is preferable that the signal processing selection unit have an analysis unit that analyzes the signal processing result of at least one of the first signal processing unit and the second signal processing unit, and the signal processing selection unit determines whether or not to cause the second signal processing unit to operate along with the first signal processing unit at the same time in accordance with a value outputted by the analysis unit.

According to this aspect, the signal processing result of at least one of the first signal processing unit and the second signal processing unit is analyzed by the analysis unit, and the signal processing selection unit can determine whether or not to cause the second signal processing unit to also operate at the same time as the first signal processing unit using the value outputted by the analysis unit. Accordingly, the sphygmograph according to this aspect is not only capable of continually saving the signal processing result of the first signal processing unit, but can also operate the second signal processing unit and save the signal processing result of the second signal processing unit at the same time as the first signal processing result in the case where further detail analysis is necessary based on the signal processing result from at least one of the first signal processing unit and the second signal processing unit, such as cases where there is a high degree of fluctuation in the DC component of the pulse wave waveform, cases where a pulse that is suspected to indicate arrhythmia is detected, and so on; it is thus possible to obtain further detailed information of the pulse.

In the sphygmograph according to the aforementioned aspects, it is preferable that the first signal processing unit extract a characteristic point from the signal outputted by the photoelectric sensor unit; the characteristic point be taken as the signal processing result of the first signal processing unit; and the second signal processing unit convert the signal outputted by the photoelectric sensor unit into a digital signal and take a signal amplitude value series as the signal processing result.

According to this aspect, the first signal processing unit extracts a characteristic point from the signal outputted by the photoelectric sensor unit, and the first signal processing unit takes the characteristic point as the signal processing result. In addition, the second signal processing unit converts the signal outputted by the photoelectric sensor unit into a digital signal, and outputs the signal processing result as a signal amplitude value time series. Accordingly, the sphygmograph according to this aspect can save the characteristic point in the signal processing result saving unit as the first signal processing unit, and the amount of data saved in the signal processing result saving unit can be reduced. Furthermore, in the case where detailed analysis is necessary by removing noise resulting from body movement or sensor shift or disturbances in the pulse due to arrhythmia, the pulse wave waveform can be recorded by the signal processing selection unit as the signal processing result of the second signal processing unit in addition to the signal processing result of the first signal processing unit, and thus further detailed analysis can be carried out.

A computer-readable medium on which is stored a program that causes a computer to function as: a first signal processing unit that processes an electric signal outputted from a photoelectric sensor unit that detects an amount of light emitted from a human body and outputs an electrical signal; a second signal processing unit having a different processing format from that of the first signal processing unit; a signal processing selection unit that determines whether or not to cause the second signal processing unit to operate along with the first signal processing unit at the same time; and a signal processing result saving unit that saves, of signal processing results of the first signal processing unit and the second signal processing unit, a signal processing result selected by the signal processing selection unit.

According to the program described in this aspect, the first signal processing unit carries out processing using the change in the amount of light emitted from the human body detected by the photoelectric sensor unit as an electrical signal and saves the result of the processing in the signal processing result saving unit, and when necessary, the signal processing selection unit causes the second signal processing unit to operate so as to process the electrical signal using the second signal processing unit; this makes it possible to save the signal processing result at the same time as the first signal processing result. Accordingly, a computer that uses the program according to this aspect can continually save the signal processing result from the first signal processing unit, and can also save the result from the second signal processing unit when necessary.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, embodiments of the present invention will be described in detail using the drawings. Note that the embodiment described hereinafter (described as a working example) is not intended to limit the invention as described in the aspects of the invention in any way. Furthermore, it is not necessarily the case that all of the elements described hereinafter are requisite elements of the invention.

Working Example 1

Figure 1:
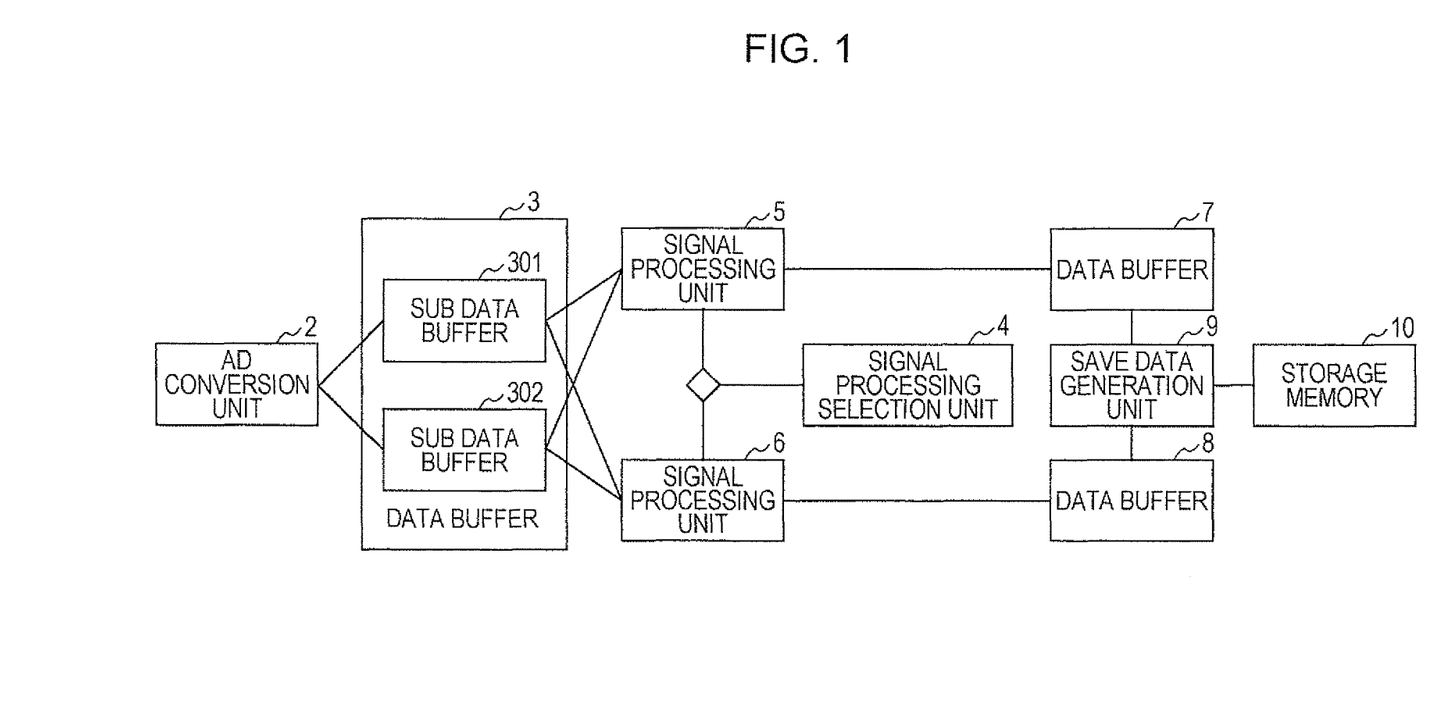
FIG. 1 is a block diagram illustrating processing functions of a sphygmograph embodying the invention.
Figure 2:
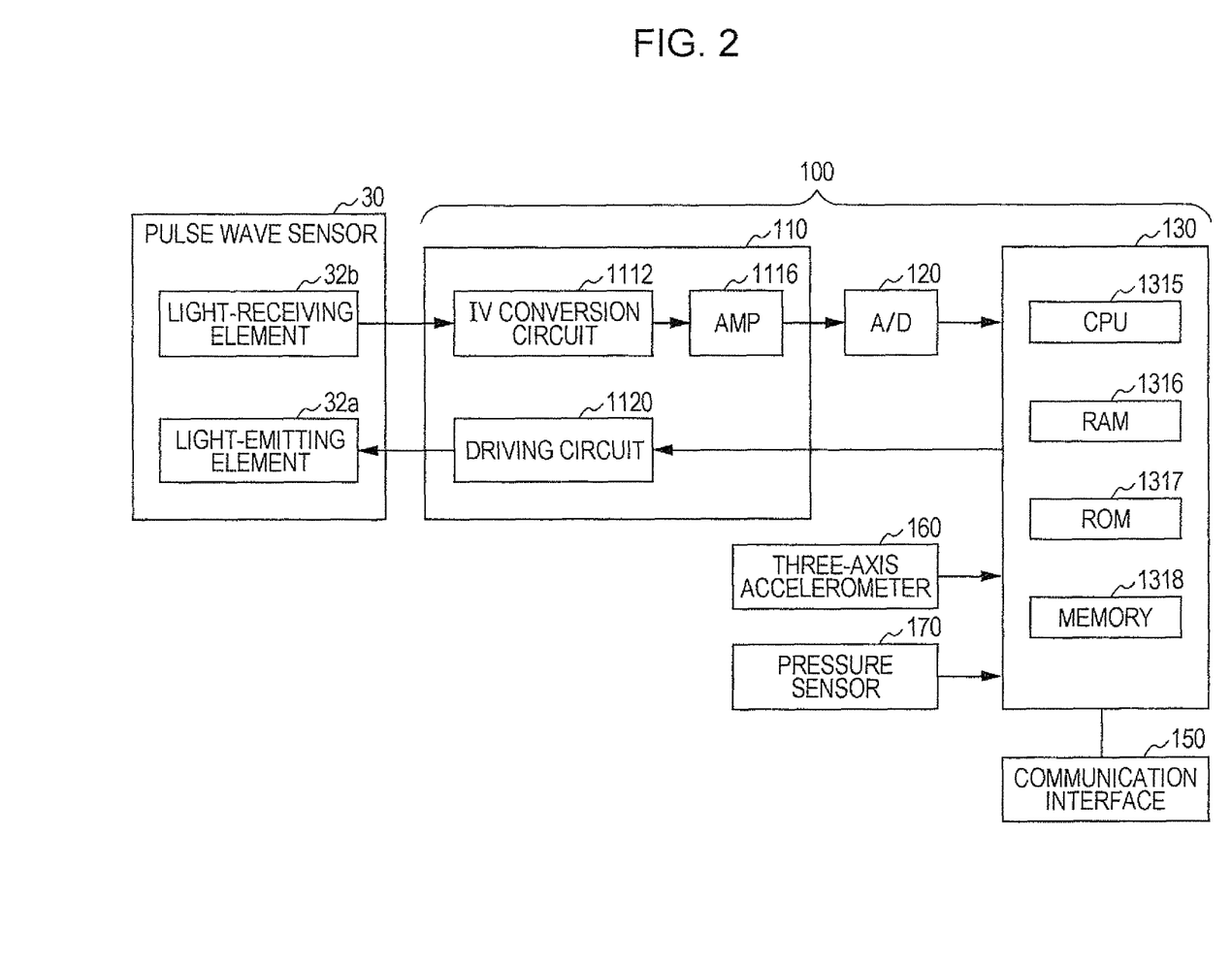
FIG. 2 is a block diagram illustrating the configuration of the sphygmograph.

FIG. 1 is a diagram illustrating the functional configuration of a sphygmograph according to Working Example 1 of the invention. FIG. 2, meanwhile, is a block diagram of the sphygmograph according to Working Example 1. Here, the modules indicate components that realize the various functions illustrated in the diagram of the functional configuration.

The sphygmograph includes an AD conversion unit 2, a data buffer 3, a signal processing selection unit 4, a signal processing unit 5, a signal processing unit 6, a data buffer 7, a data buffer 8, a save data generation unit 9, and a storage memory 10.

The AD conversion unit 2 controls an A/D conversion circuit 120; the AD conversion unit 2, the signal processing selection unit 4, the signal processing unit 5, the signal processing unit 6, and the save data generation unit 9 are stored as parts of a program recorded in a ROM 1317, and are executed by a CPU 1315. The data buffer 3, the data buffer 7, and the data buffer 8 are secured in a specific region of a RAM 1316, and are managed by the CPU 1315. A memory 1318 is, for example, a high-capacity non-volatile rewritable memory having a capacity of approximately 32 megabytes, and is used as the storage memory 10.

Figure 3:
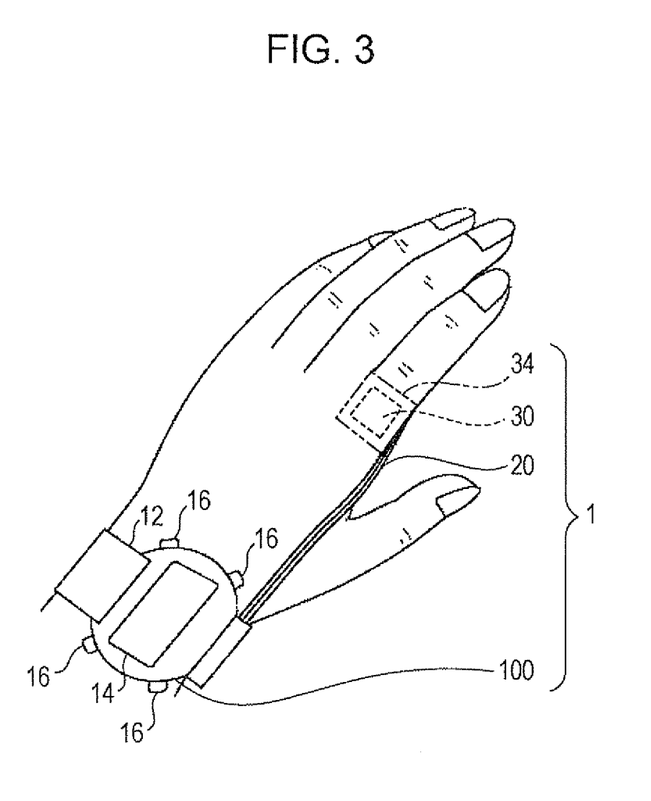
FIG. 3 is an external view of the sphygmograph.

FIG. 3 is an external view of a sphygmograph 1. As shown in FIG. 3, the sphygmograph 1 includes a pulse wave sensor 30, a main apparatus unit 100, and a cable 20 that connects the two. The pulse wave sensor 30 fulfills the role of a detection unit, taking the index finger on the left hand of a user as a measurement area and detecting volumetric changes in a blood vessel in that area arising due to the flow of blood through the blood vessel as biological information. The pulse wave sensor 30 is a flat, plate-shaped component whose dimensions are smaller than the width of the index finger on the left hand. The pulse wave sensor 30 has both a light-emitting element 32a and a light-receiving element 32b. The light-emitting element 32a is a light-emitting diode (LED) that emits light of a color at a wavelength that can be easily absorbed by blood (for example, blue). The light-receiving element 32b is a photodiode. A sensor securing band 34 is attached to the pulse wave sensor 30.

The pulse wave sensor 30 is worn on the user's body by wrapping the sensor securing band 34 around the measurement area with the light-emitting element 32a and the light-receiving element 32b facing the measurement area. When worn in this state, the light-emitting element 32a of the pulse wave sensor 30 irradiates the measurement area with light of an intensity based on a current supplied to the light-emitting element 32a from the main apparatus unit 100 via the cable 20. The light irradiated from the light-emitting element 32a passes through the epidermis of the measurement area and reaches a capillary blood vessel in the hypodermis therebehind. Some of the light that has reached the blood vessel is absorbed by the blood that flows within the blood vessel. Meanwhile, some of the light that reached the blood vessel but was not absorbed by the blood flowing in the blood vessel passes through the measurement area, whereas the remainder is diffused throughout the biological structures and returns to the light-receiving element 32b as reflected light. A current of a magnitude that is based on the optical intensity of this received reflected light flows in the light-receiving element 32b. Here, the blood vessel in the measurement area repeatedly expands and contracts at the same cycle as the heartbeat. As a result, the amount of absorbed light increases and decreases with the same cycle as the expansion and contraction of the blood vessel, which also causes the intensity of the reflected light to change. Accordingly, the current that flows in the light-receiving element 32b has a component that indicates volumetric changes in the blood vessel in the measurement area.

The main apparatus unit 100 has a shape similar to that of a wristwatch. A display unit 14 having a rectangular display surface is provided on the top surface of the main apparatus unit 100. The display unit 14 displays a pulse interval, a pulse frequency, and other types of information that are the result of the measurement performed by the sphygmograph 1. Button switches 16 are provided in an outer circumferential portion of a housing of the main apparatus unit 100. The button switches 16 are used to input various instructions, such as starting and stopping the measurement of pulse waves, resetting the measurement results, and so on. Two respective ends of a wristband 12 are attached to opposing sides of the outer circumferential portion of the main apparatus unit 100, on opposite sides of the display unit 14. The main apparatus unit 100 is worn on the body of the user by wrapping the wristband 12 around the wrist of the user.

As shown in FIG. 2, the main apparatus unit 100 of the sphygmograph 1 includes a communication interface 150, an analog circuit portion 110, the A/D conversion circuit 120, a three-axis accelerometer 160, a pressure sensor 170, and a control circuit portion 130. The communication interface 150 is a unit that carries out wireless communication through Bluetooth®. The main apparatus unit 100 is connected to a personal computer through the communication interface 150. The analog circuit portion 110 includes a driving circuit 1120, an IV conversion circuit 1112, and an amplifier 1116. The driving circuit 1120 is a circuit that drives the light-emitting element 32a of the pulse wave sensor 30. Under the control of the control circuit portion 130, the driving circuit 1120 supplies a current to the light-emitting element 32a of the pulse wave sensor 30. Through this, the light-emitting element 32a irradiates the measurement area with light, and the current that flows in the light-receiving element 32b changes based on the optical intensity of the received reflected light. The reason the current that flows in the light-receiving element 32b has a component that indicates volumetric changes in the blood vessel of the measurement area is as described above. The IV conversion circuit 1112 outputs, to the amplifier 1116, a voltage based on the current that flows in the light-receiving element 32b. The amplifier 1116 amplifies the voltage outputted by the IV conversion circuit 1112, and outputs the amplified signal to the A/D conversion circuit 120.

The A/D conversion circuit 120 converts the signal outputted by the amplifier 1116 into a digital format, and outputs the converted signal to the control circuit portion 130. The control circuit portion 130 is a unit that fulfills the role of control center for the sphygmograph 1. The control circuit portion 130 includes a central processing unit (CPU) 1315, a random access memory (RAM) 1316, a read-only memory (ROM) 1317, and an electrically-erasable programmable read-only memory (EEPROM) 1318.

The A/D conversion circuit 120 performs digital data conversion at a timing controlled by the AD conversion unit 2. The AD conversion unit 2 uses, for example, a sampling rate of 50 Hz and a quantization strength of 10 bits or the like.

The three-axis accelerometer 160 has a structure in which a pivoting portion that serves as a spindle is loosely anchored in a neutral position, and is an accelerometer, with three detection axes, that detects displacement of the spindle through electrostatic capacitance, piezoelectric resistance, or the like. The detected displacement is obtained as an electrical signal, but through A/D conversion is converted to digital data that can be processed by the CPU 1315 and outputted. For example, the accelerations in the X, Y, and Z axes are outputted as 10 bit unsigned integers. The three-axis accelerometer 160 is contained within the sphygmograph 1 and is used in order to detect the displacement of the sphygmograph 1.

The pressure sensor 170 includes a fixed electrode and a mobile electrode that are opposed to each other, and converts a change in electrostatic capacitance arising when the mobile electrode deforms due to an external pressure into an electrical signal. Furthermore, the signal is converted, through A/D conversion, into digital data that can be processed by the CPU 1315, and is then outputted. For example, a 10 bit unsigned integer is outputted. The pressure sensor 170 is disposed on the side of the pulse wave sensor 30 that makes contact with a finger, so as to be capable of measuring contact pressure between the finger and the pulse wave sensor 30.

The sphygmograph 1 has three modes, or a measurement mode, a communication mode, and a standby mode. These modes can be switched by using the button switches 16. Incidentally, the standby mode corresponds to a mode in which no particular processing is carried out.

Operations performed after switching to the measurement mode using the button switches 16 will be described hereinafter.

The data outputted from the AD conversion unit 2 is recorded in the data buffer 3 with each sample. This operation will be described in detail next.

The CPU 1315 operates the AD conversion unit 2 every 20 ms. When the AD conversion unit 2 writes an instruction for the A/D conversion circuit 120 to carry out an AD conversion process into a register, the AD conversion is commenced, and the result is written into the register. The A/D conversion circuit 120 and the CPU 1315 are also connected by an interrupt signal line, and the CPU 1315 detects that the A/D conversion circuit 120 has finished processing from an end interrupt signal from the A/D conversion circuit 120. Upon detecting the end interrupt from the A/D conversion circuit 120, the CPU 1315 reads out the conversion result data from the register of an AD converter through the AD conversion unit 2, and saves that data in the data buffer 3 provided in the RAM 1316. For example, with the register provided in the A/D conversion circuit 120, data can be accessed by a CPU 11 and programs through addressing using a memory-mapped IO method, in the same manner as RAM access.

The AD conversion unit 2 confirms the roles of sub data buffers 301 and 302 in the data buffer 3 each time data is to be saved in the data buffer 3, and saves the data in the sub data buffer that serves as an AD conversion recording region. A descriptor of the role of the sub data buffer is held as a variable in a region in the RAM 1316. When a certain amount A of data has been saved in the data buffer 3, the signal processing selection unit 4 is notified that the signal saving is complete.

Here, it is desirable for the certain amount A to be a size that is within half of the memory size allocated to the data buffer 3 and is appropriate for measurement time segments. For example, in the case where the capacity of the data buffer 3 is two kilobytes, the region is divided into two sections of one kilobyte each. For the sake of simplicity, these regions are called the sub data buffer 301 and the sub data buffer 302. Assuming that at a given point in time the sub data buffer 301 is a region for saving signals by the AD conversion unit 2 and the sub data buffer 302 is a signal processing data region, and furthermore a 10 bit AD conversion result is extended to 16 bits and AD conversion is carried out at 20 Hz as a format for recording the result of the AD conversion in the data buffer 3, it is desirable to define the certain amount A as 1,000 bytes, corresponding to 10 seconds' worth of data.

Next, operations performed by the signal processing selection unit 4 will be described.

Upon receiving a notification from the AD conversion unit 2 that signal saving has ended, the signal processing selection unit 4 clears a signal save in progress flag. The signal save in progress flag is held as a variable in a region of the RAM 1316. Likewise, in the case where both signal processes performed by the signal processing unit 5 and the signal processing unit 6 have ended, a signal process in progress flag is cleared by receiving one or two, that is, as many as necessary, signal processing end notifications from the signal processing unit 5 and the signal processing unit 6. The signal process in progress flag is also held as a variable in a region of the RAM 1316.

In the case where both the signal process in progress flag and the signal save in progress flag have been cleared, the signal processing selection unit 4 switches the roles of the sub data buffer 301 and the sub data buffer 302 in the data buffer 3. Specifically, in the case where the sub data buffer 301 is set to the role of a AD conversion recording region and the sub data buffer 302 is set to the role of a signal processing data region, the sub data buffer 301 is switched to a signal processing data region and the sub data buffer 302 is switched to an AD conversion recording region at this timing. In the case where the roles of the sub data buffers 301 and 302 are reversed and are to be switched, the sub data buffer 301 is set to the AD conversion recording region and 302 to the signal processing data region. As described earlier, these roles are held as variables in regions of the RAM 1316, and are realized by setting these values. At the same time as the roles of the sub data buffers are changed, the signal processing selection unit 4 instructs the signal processing unit 5 and the signal processing unit 6 of signal processes to be commenced according to a signal processing selection method, and sets the signal process in progress flag and the signal save in progress flag.

Hereinafter, details will be given regarding operations performed in the signal processing selection method of the signal processing selection unit 4.

The signal processing selection unit 4 controls the three-axis accelerometer 160, and obtains acceleration data every 20 ms. Assuming that the X-axis acceleration, the Y-axis acceleration, and the Z-axis acceleration at a given time t ms are expressed as Xg(t), Yg(t), and Zg(t), respectively, the signal processing selection unit 4 calculates an acceleration index G(t) each time through the following Formula (1).

$$G(t) = f(Ax \times Xg(t) \times Xg(t) + Ay \times Yg(t) \times Yg(t) + Az \times Zg(t) \times Zg(t)) \quad (1)$$

Here, the function f(x) is the square root of x. Weighting coefficients Ax, Ay, and Az are values for changing the priority of the axes based on the attachment direction, but here it may be assumed that Ax=Ay=Az=1. Furthermore, at the same time, an average value GAveSec of the most recent 50 times including the time t, or G(t−980), G(t−960), and so on up to G(t), is calculated. In addition, an average value GAveMin of the most recent 3,000 times including the time t, or G(t−59980), G(t−59960), and so on up to G(t), is calculated. At the same time, the signal processing selection unit 4 sets a second processing unit operation request flag FL1 when the average value GAveSec of G( ) in one second is greater than or equal to 1. Conversely, when GAveSec is less than 1, the second processing unit operation request flag FL1 is cleared. At the same time, the signal processing selection unit 4 sets a second processing unit operation request flag FL2 when the average value GAveMin of G( ) in one minute is less than 0.001. Conversely, when GAveMin is greater than or equal to 0.001, the second processing unit operation request flag FL2 is cleared. The second processing unit operation request flag FL1 and the second processing unit operation request flag FL2 are variables held in a region of the RAM 1316.

The signal processing selection unit 4 determines whether or not to instruct the signal processing unit 6 to start signal processing through the following method.

Operations are described for combinations of the following conditions:

(C1) when the second processing unit operation request flag FL1 is set; and (C2) when the second processing unit operation request flag FL2 is set.

(A1) When C1 is true and C2 is false, the signal processing unit 6 is instructed to start signal processing.

(A2) When C1 and C2 are true, and an FL2Count, which is a variable held in the RAM 1316, is less than or equal to 30, the signal processing selection unit 4 adds 1 to the FL2Count, and the signal processing unit 6 is instructed to start signal processing.

(A3) When C1 and C2 are false, FL2Count is set to 0. The signal processing unit 6 is not instructed to start signal processing.

(A4) When C1 is false and C2 is true, and FL2Count is less than or equal to 30, 1 is added to the FL2Count, and the signal processing unit 6 is instructed to start signal processing.

It is assumed that the signal processing selection unit 4 always instructs the signal processing unit 5 to start the signal processing.

Meanwhile, the signal processing selection unit 4 controls the pressure sensor 170 and obtains pressure data every 20 ms. The pressure at the given time t ms is taken as P(t). The signal processing selection unit 4 sets a second processing unit operation request flag FL3 when P(t) is less than or equal to 10 mmHg or greater than or equal to 30 mmHg. Otherwise, FL3 is cleared. The second processing unit operation request flag FL3 is a variable held in a region of the RAM 1316.

The signal processing selection unit 4 determines whether or not to instruct the signal processing unit 6 to start signal processing through the following method. However, the method is not limited thereto in the case where instructing the start of signal processing through determinations using the accelerometer is valid.

In the case where the second processing unit operation request flag FL3 is set, the signal processing unit 6 is instructed to start signal processing. In the case where the second processing unit operation request flag FL3 is cleared, the signal processing unit 6 is not instructed to start signal processing.

Meanwhile, the signal processing selection unit 4 analyzes an RR interval series outputted to the data buffer 7 by the signal processing unit 5, and in the case where the standard deviation of the RR interval data series exceeds 100 ms, a second processing unit operation request flag FL4 is set. Otherwise, FL4 is cleared. The second processing unit operation request flag FL4 is a variable held in a region of the RAM 1316.

The signal processing selection unit 4 determines whether or not to instruct the signal processing unit 6 to start signal processing through the following method. However, the method is not limited thereto in the case where instructing the start of signal processing through determinations using the accelerometer and the pressure sensor is valid.

In the case where the second processing unit operation request flag FL4 is set, the signal processing unit 6 is instructed to start signal processing. In the case where the second processing unit operation request flag FL4 is cleared, the signal processing unit 6 is not instructed to start signal processing.

Next, the signal processing unit 5 and the signal processing unit 6 that receives signal processing start instructions from the signal processing selection unit 4 carry out signal processing on the data which resides in a region that corresponds to the signal processing data region of the sub data buffer 301 and the sub data buffer 302 in the data buffer 3, and save the signal processing results in the data buffer 7 and the data buffer 8, respectively. Upon completing the processes on the data in the respective buffers in the data buffer 3, the signal processing unit 5 and the signal processing unit 6 notify the signal processing selection unit 4 of the completion.

Next, the signal processes performed by the signal processing unit 5 and the signal processing unit 6 will be described in detail. An example in which the signal processing unit 5 performs a peak interval detection process and the signal processing unit 6 performs a pulse wave component signal detection process will be described.

First, the peak detection process performed by the signal processing unit 5 will be described. The data in the signal processing data region of the sub data buffer that is to be processed is 10 seconds' worth of data. This data is analyzed as a time-series sample with a 16-bit integer value from the start, and a smoothing process is first carried out on all samples. A Savitzky-Golay algorithm may be used in the smoothing process. After the smoothing has been carried out, a first-order differential data string is created for all samples, and all times at which the differential value is 0 are found. The times are found taking into consideration that the time between samples is 20 ms, assuming that the first sample time at the beginning of measurement is 0, then those times are saved as a series of pole times. For example, if Ncycle is taken as the total number of times the AD conversion unit 2 has filled the data storage buffer, (0+10×Ncycle) seconds is the time of the starting sample for the data currently present in the signal processing region.

Next, an example of a method for finding a zero point will be described. In the case where a sample string with a length of 3 starting from time t is (1, 0, −1), it is assumed that t 20 ms is the time when the differential value is 0. Meanwhile, with a sample string of a length N 2 that includes non-zero samples that surround a plurality of (N) sequential 0s, a sample string of a length of 2 with no 0s and inverting signs, and so on, if the start of the sample string is taken as time t and the length of the sample string is taken as a length M, Tzero found according to the following Formula (2) is taken as the time when the differential value is 0.

$$Tzero = t + (0 + 20 \times (M-1))/2 \qquad (2)$$

At the same time, a second-order differential process is carried out on all the samples, a second-order differential data series is created, and that each time in the pole point time series, the second-order differential value is extracted only in the case where that value is negative. The post-extraction time series is taken as a peak time series. Next, a time interval of the peak time series is found, and an RR interval series is created. At this time, the final peak time is recorded in the RAM 1316 as a "previous final peak time." In the case where the "previous final peak time" is stored, the initial RR interval is calculated from the initial peak time, and the data is added to the start of the RR interval series. The RR interval series is recorded in the data buffer 7.

Figure 4:
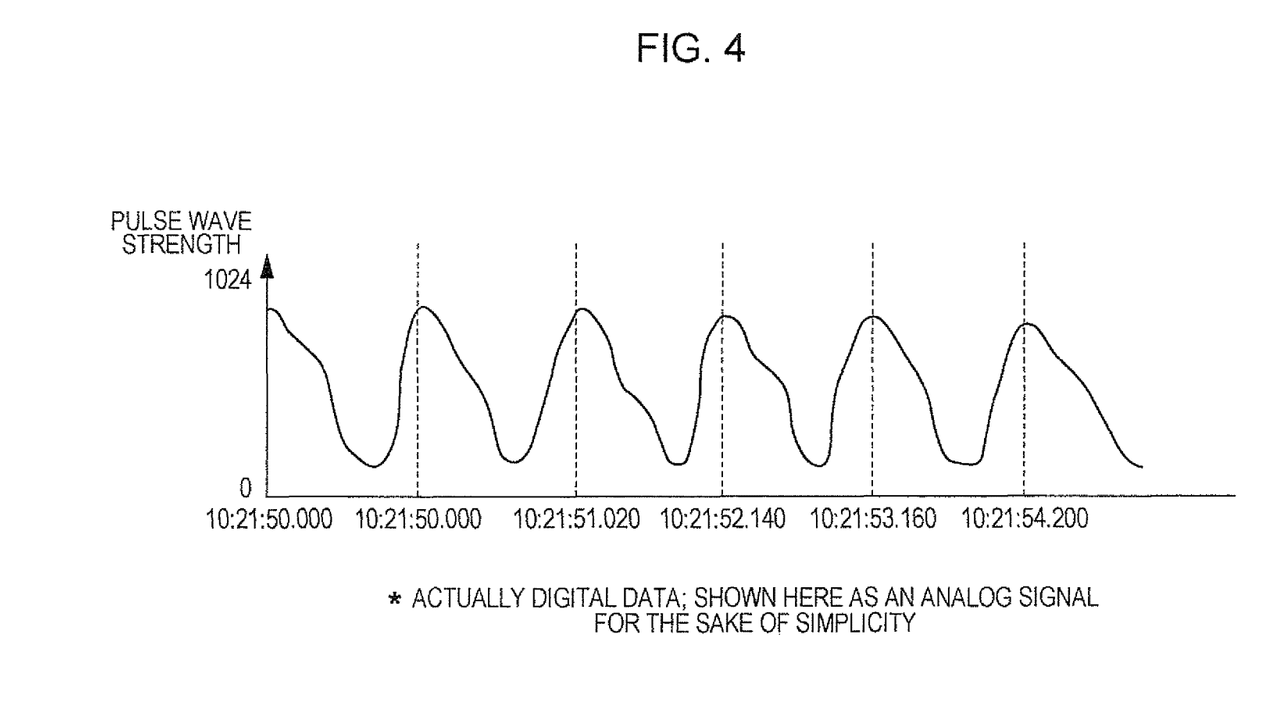
FIG. 4 is an example of pulse wave data obtained by a pulse wave sensor in the sphygmograph.
Figure 5:
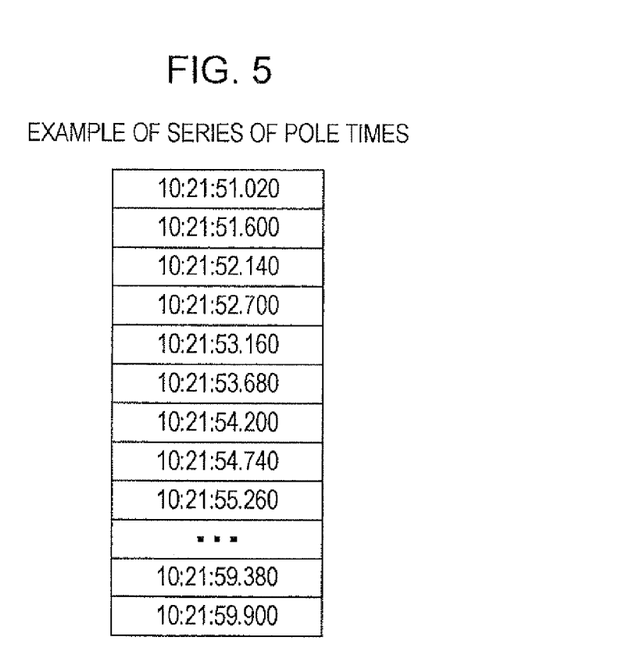
FIG. 5 is a diagram illustrating an example of pole time series data processed by the sphygmograph.
Figure 6:
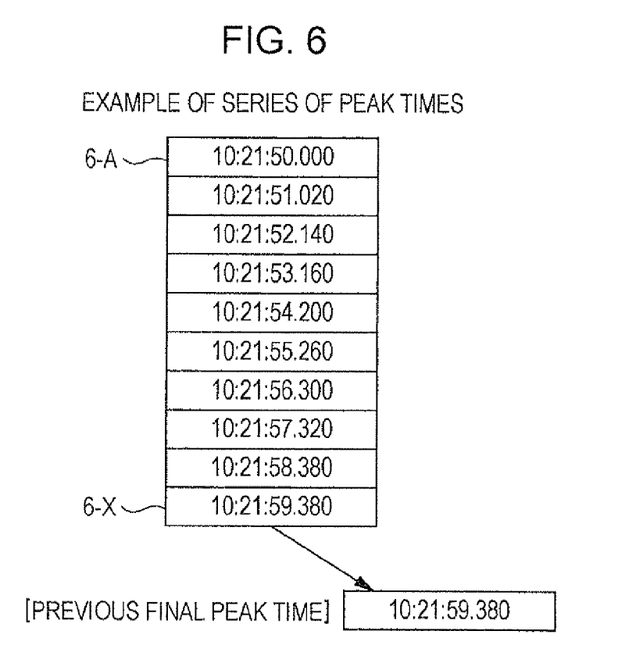
FIG. 6 is a diagram illustrating an example of peak time series data processed by the sphygmograph.
Figure 7:
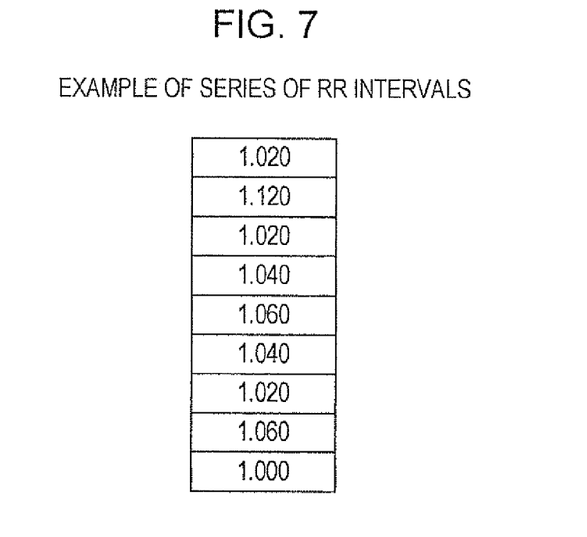
FIG. 7 is a diagram illustrating an example of an RR interval series processed by the sphygmograph.

For example, in the case of a sample data string that can be plotted as shown in FIG. 4, a series of pole times such as that shown in FIG. 5 is generated. Next, peaks are extracted as shown in FIG. 6, and a peak time series is generated. The final peak time in FIG. 6 (the data located at the position 6-X; the position of X from the start may change depending on the circumstances) is used as the position 6-A as the starting peak time in the next sample. FIG. 7 illustrates an RR interval series found from the peak time series shown in FIG. 6.

As a process for detecting peaks performed by the signal processing unit, the aforementioned first-order differential data series of the samples is created, after which a time of the peak point of the first-order differential data is found; a time series thereof (that is, a first-order differential peak time series) is created, and the interval of that time series may then be used as the RR interval series.

The pulse wave component signal detection process performed by the signal processing unit 6 will now be described. The data in the signal processing data region of the sub data buffer that is to be processed is 10 seconds' worth of data. This data is analyzed as a time-series sample with a 16-bit integer value from the start, and a Savitzky-Golay algorithm is applied to all samples. At this time, it is desirable to use an algorithm that carries out parameter adjustment so that high-frequency components of greater than or equal to 3 Hz are removed. The result of this process is recorded in the data buffer 8. Although the number of samples and the data format of the data generated for the data buffer 8 by the signal processing unit 6 is the same as that of the original data, the values thereof are different.

Here, it is desirable for the signal processing unit 5 and the signal processing unit 6 to end the signal processes and to clear the signal process in progress flag before the AD conversion unit 2 fills the data storage buffer and the signal save in progress flag is cleared. Doing so makes it possible for the AD conversion unit 2 to continuously use the data storage buffer, which makes it possible to obtain biological data without any data loss.

The signal processing unit 5 may densify the data using spline interpolation or the like prior to carrying out the smoothing. Doing so makes it possible to improve the accuracy of the peak time detection. However, because priority is placed on carrying out processing faster than the processing performed by the AD conversion unit 2 as described earlier, it is desirable to use a densification method in which processing is sufficiently simple.

Next, operations performed by the signal processing selection unit 4 and the save data generation unit 9 after the result of processing the certain amount of data has been stored in the data buffer 7 and the data buffer 8 will be described. Upon detecting that the signal process in progress flag has been cleared, indicating the processing performed by the signal processing unit 5 or the signal processing unit 6 has ended, the signal processing selection unit 4 instructs the save data generation unit 9 to start a saving process. Upon receiving the instruction, the save data generation unit 9 adds data to a file 7-F corresponding to the data buffer 7 and a file 8-F corresponding to the data buffer 8. The file 7-F and the file 8-F are created by the save data generation unit 9 when the mode is changed to the measurement mode through operations performed using the button switches 16 and an instruction to start the saving process is made immediately after the measurement is started.

Figure 9:
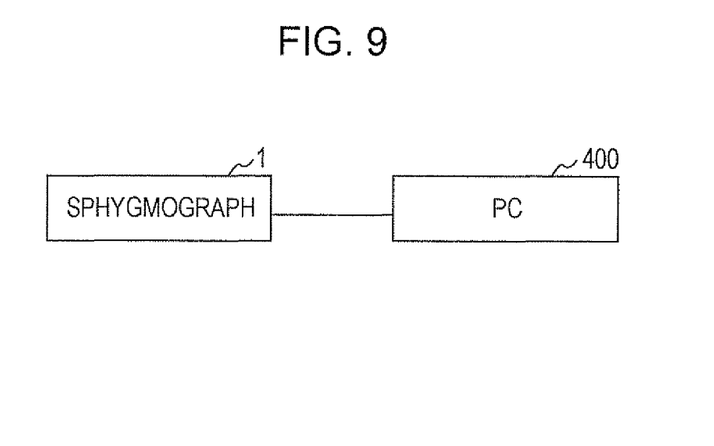
FIG. 9 is a block diagram illustrating a case where the sphygmograph communicates with a PC.

Next, operations performed when the sphygmograph 1 is set to the communication mode using the button switches 16 and communicates with a PC will be described. Note that FIG. 9 illustrates the relationship between the sphygmograph 1 and a PC 400, where the sphygmograph 1 and the PC 400 are connected through, for example, the Bluetooth serial port profile (SPP). In this state, biological information data saved in the sphygmograph 1 is transferred to the PC 400.

Figure 10:
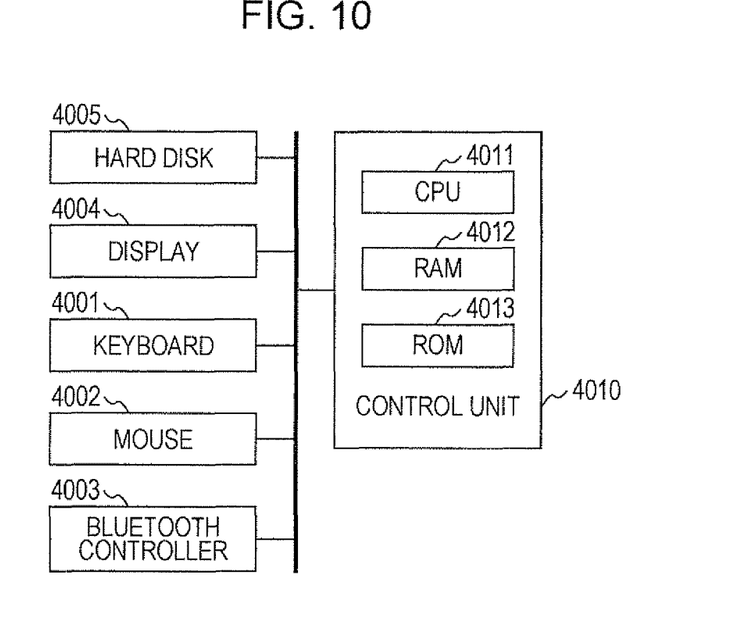
FIG. 10 is a block diagram illustrating the configuration of a PC that communicates with the sphygmograph.

FIG. 10 is a block diagram illustrating the configuration of the PC 400. The PC 400 includes a control unit 4010, a hard disk 4005, a display 4004, a keyboard 4001, a mouse 4002, and a Bluetooth® controller 4003. The control unit 4010 is configured of a CPU 4011, a RAM 4012, a ROM 4013, or the like. The CPU 4011 executes various programs stored in the ROM 4013, the hard disk 4005, and the like, using the RAM 4012 as a work area. A control program is stored in the hard disk 4005. This control program carries out a data transfer process.

When the sphygmograph 1 is set to a communication standby mode, the control circuit portion 130 of the sphygmograph 1 sets the communication interface 150 to a connection standby state. When an operation instructing data transfer to be carried out is made using the keyboard 4001, the mouse 4002, or the like of the PC 400 in this state, the control unit 4010 of the PC 400 sets the Bluetooth controller 4003 into a communicable state; when the Bluetooth controller 4003 is connected to the communication interface 150, the communication interface 150 enters a connected state, and the Bluetooth controller 4003 also enters a connected state. Note that it is assumed that the sphygmograph 1 and the PC 400 have a serial port connection at this time, in accordance with the Bluetooth SPP communication specification.

Figure 8:
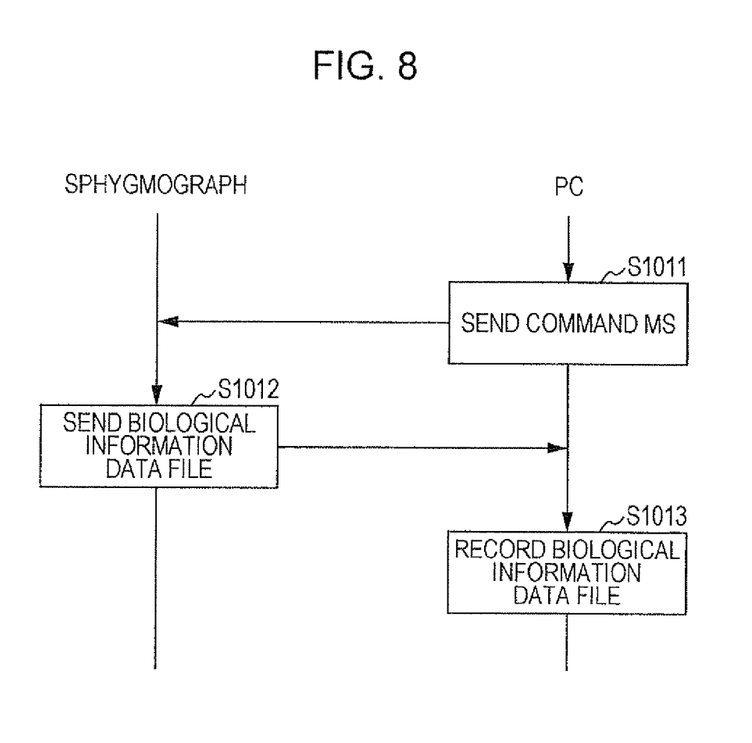
FIG. 8 is a flowchart illustrating a data transfer process carried out when the sphygmograph communicates with a PC.

FIG. 8 is a flowchart illustrating a data transfer process.

In the data transfer process, when an operation instructing a data transfer has been made, the CPU 4011 of the PC 400 transfers a command CM to the sphygmograph 1 (S1011). The CPU 1315 of the sphygmograph 1 reads out the file 7-F or the file 8-F of the storage memory 10 from the memory 1318 and transfers that file to the PC 400 via the wireless connection (S1012). Although this transfer is carried out here according to a binary transfer protocol such as XMODEM, the transfer is not limited to this method. The CPU 4011 of the PC 400 saves the biological information file 7-F or file 8-F transferred from the sphygmograph 1 into the hard disk 4005 (S1013).

Although Bluetooth has been described as used in the data transfer process, USB may be used instead; any communication means may be used as long as it is capable of transferring binary files.

In addition, although a communication tool including Bluetooth has been described, the memory 1318 of the sphygmograph 1 may be a removable medium such as, for example, an SD card. In this case, if the PC 400 is provided with an SD card media reader, the file 7-F and the file 8-F can be directly read by the media reader.

What is claimed is:
1. A sphygmograph comprising:
a photoelectric sensor unit that detects an amount of light emitted from a human body and outputs an electrical signal;

a first signal processing unit that performs a signal process on the signal outputted from the photoelectric sensor unit;

a second signal processing unit that performs a signal process on the signal outputted from the photoelectric sensor unit in a different process from that of the first signal processing unit;

a signal processing selection unit that determines whether or not to cause the second signal processing unit to operate along with the first signal processing unit in parallel at the same time; and a signal processing result saving unit that saves, of signal processing results of the first signal processing unit and the second signal processing unit, a signal processing result selected by the signal processing selection unit.

2. The sphygmograph according to claim 1,
wherein the signal processing selection unit includes:
a motion sensor unit that detects a motion amount of the human body and outputs a signal; and
a motion signal processing unit that performs a signal process on the signal outputted from the motion sensor unit, and
the signal processing selection unit determines whether or not to cause the second signal processing unit to operate along with the first signal processing unit in parallel at the same time in accordance with a value outputted by the motion signal processing unit.

3. The sphygmograph according to claim 1,
wherein the signal processing selection unit includes:
a shift sensor unit that detects an amount by which the photoelectric sensor shifts from the human body and outputs a signal; and
a shift signal processing unit that performs a signal process on the signal outputted from the shift sensor unit, and
the signal processing selection unit determines whether or not to cause the second signal processing unit to operate along with the first signal processing unit in parallel at the same time in accordance with a value outputted by the shift signal processing unit.

4. The sphygmograph according to claim 1,
wherein the signal processing selection unit includes:
an analysis unit that analyzes the signal processing result of at least one of the first signal processing unit and the second signal processing unit, and
the signal processing selection unit determines whether or not to cause the second signal processing unit to operate along with the first signal processing unit in parallel at the same time in accordance with a value outputted by the analysis unit.

5. The sphygmograph according to claim 1,
wherein the first signal processing unit extracts a characteristic point from the signal outputted by the photoelectric sensor unit;
the characteristic point is taken as the signal processing result of the first signal processing unit; and
the second signal processing unit converts the signal outputted by the photoelectric sensor unit into a digital signal and takes a signal amplitude value series as the signal processing result.

6. A non-transitory computer-readable medium on which is stored a program that causes a computer to function as:
a first signal processing unit that processes an output signal outputted from a photoelectric sensor unit that detects an amount of light emitted from a human body and outputs an electrical signal;
a second signal processing unit having a different processing format from that of the first signal processing unit;
a signal processing selection unit that determines whether or not to cause the second signal processing unit to operate along with the first signal processing unit in parallel at the same time; and
a signal processing result saving unit that saves, of signal processing results of the first signal processing unit and the second signal processing unit, a signal processing result selected by the signal processing selection unit.

\* \* \* \* \*